US007563782B2

(12) United States Patent
Masuda et al.

(10) Patent No.: US 7,563,782 B2
(45) Date of Patent: Jul. 21, 2009

(54) T-TYPE CALCIUM CHANNEL BLOCKER

(75) Inventors: Yukinori Masuda, Chiyoda-ku (JP); Taiji Furukawa, Saitama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 262 days.

(21) Appl. No.: 10/549,510

(22) PCT Filed: Mar. 29, 2004

(86) PCT No.: PCT/JP2004/004432

§ 371 (c)(1), (2), (4) Date: Sep. 20, 2005

(87) PCT Pub. No.: WO2004/087172

PCT Pub. Date: Oct. 14, 2004

(65) Prior Publication Data
US 2007/0010490 A1 Jan. 11, 2007

(30) Foreign Application Priority Data
Mar. 28, 2003 (JP) ............... 2003-090916
Nov. 25, 2003 (JP) ............... 2003-393893

(51) Int. Cl.
A61K 31/675 (2006.01)
C07F 9/02 (2006.01)
(52) U.S. Cl. .......................... 514/89; 546/21
(58) Field of Classification Search ................. 514/89; 546/21; 544/337
See application file for complete search history.

(56) References Cited

U.S. PATENT DOCUMENTS 4,535,073 A * 8/1985 Kimura et al. ............. 514/89
4,885,284 A 12/1989 Seto et al.

FOREIGN PATENT DOCUMENTS

| EP | 0 500 426 A1 | 8/1992 |
|----|----|----|
| EP | 0 599 220 A1 | 6/1994 |
| JP | A-59-161392 | 9/1984 |
| JP | A-60-069089 | 4/1985 |
| JP | A-60-248693 | 12/1985 |
| JP | A-60-258194 | 12/1985 |
| JP | A-61-030591 | 2/1986 |
| JP | A-61-37793 | 2/1986 |
| JP | A-61-063688 | 4/1986 |
| JP | A-61-210092 | 9/1986 |
| JP | A-61-254569 | 11/1986 |
| JP | A-62-169795 | 7/1987 |
| JP | A-62-169796 | 7/1987 |
| JP | A-62-195392 | 8/1987 |
| JP | A-63-68591 | 3/1988 |
| JP | A-63-233992 | 9/1988 |
| JP | A-1-113398 | 5/1989 |
| JP | A-01-275591 | 11/1989 |

| WO | WO 01/04124 A1 | 1/2001 |
|----|----|----|

OTHER PUBLICATIONS

Haruko Masumiya et al.; "Effects of $Ca^{2+}$ channel antagonists on sinus node: Prolongation of late phase 4 depolarization by efonidipine"; *European Journal of Pharmacology*; vol. 335; 1997; pp. 15-21.

Paul Mulder et al.; "Increased Survival After Long-Term Treatment with Mibefradil, a Selective T-Channel Calcium Antagonist, in Heart Failure"; *JACC*; vol. 29, No. 2; Feb. 1997; pp. 416-421.

(Continued)

Primary Examiner—Charanjit S Aulakh
(74) Attorney, Agent, or Firm—Oliff & Berridge, Plc.

(57) ABSTRACT

There is provided a T-type calcium channel blocker that is optically active 1,4-dihydropyridine compound, a pharmaceutically acceptable salt thereof or a solvate thereof, of formula (1)

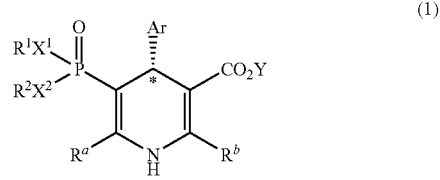

(1)

wherein $R^1$ and $R^2$ are independently of each other $C_{1-6}$ alkyl group or $R^1$ and $R^2$ together form $-CR^5R^6-CR^7R^8-$, $-CR^5R^6-CR^7R^8-CR^9R^{10}-$ or $-CR^5R^6-CR^7R^8-CR^9R^{10}-CR^{11}R^{12}-$, etc., $X^1$ and $X^2$ are independently of each other O or $NR^{13}$, Ar is optionally substituted phenyl group, etc., $R^a$ and $R^b$ are independently of each other $C_{1-6}$ alkyl group, $-L^2-NR^{16}R^{17}$, $CH_2O-L^2-NR^{16}R^{17}CN$, $-L^2-N(CH_2CH_2)_2NR^{16}$ or $NR^{16}R^{17}$, etc., Y is $C_{1-20}$ alkyl group, $-L^3-NR^{18}R^{19}$

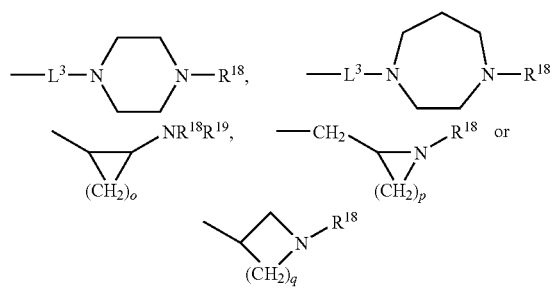

and * is absolute configuration of R.

6 Claims, No Drawings

OTHER PUBLICATIONS

Johanne Villame et al.; "Effects of Mibefradil, a T- and L-Type Calcium Channel Blocker, on Cardiac Remodeling in the UM-X7.1 Cardiomyopathic Hamster"; *Cardiovascular Drugs and Therapy*; vol. 15; 2001; pp. 41-48.

Samir Fareh et al.; "The T-Type $Ca^{2+}$ Channel Blocker Mibefradil Prevents the Development of a Substrate for Atrial Fibrillation by Tachycardia-Induced Atrial Remodeling in Dogs"; *Circulation*; vol. 100; Nov. 23, 1999; pp. 2191-2197.

Georg Noll et al.; "Comparative Pharmacological Properties among Calcium Channel Blockers: T-Channel versus L-Channel Blockade"; Cardiology; vol. 89; Supp. 1; 1998; pp. 10-15.

Chris Baylis et al.; "Comparison of L-Type and Mixed L- and T-Type Calcium Channel Blockers on Kidney Injury Caused by Deoxycorticosterone-Salt Hypertension in Rats"; *American Journal of Kidney Diseases*; vol. 38, No. 6; 2001; pp. 1292-1297.

D. Bilici et al.; "Protective Effect of T-Type Calcium Channel Blocker in Histamine-Induced Paw Inflammation in Rat"; *Pharmacological Research*; vol. 44, No. 6; 2001; pp. 527-531.

Sebastien Lenglet et al.; "Activation of 5-$HT_7$ Receptor in Rat Glomerulosa Cells is Associated with an Increase in Adenylyl Cyclase Activity and Calcium Influx through T-Type Calcium Channels"; Endocrinology; vol. 143, No. 5; pp. 1748-1760.

J. Bruce McCallum et al.; "Loss of T-type Calcium Current in Sensory Neurons of Rats with Neuropathic Pain"; *Anesthesiology*; vol. 98, No. 1; 2003; pp. 209-216.

Darrell M. Porcello et al.; "Actions of U-92032, a T-Type $CA^{2+}$ Channel Antagonist, Support a Functional Linkage Between $I_T$ and Slow Intrathalamic Rhythms"; *Journal of Neurophysiology*; vol. 89; Jan. 2003; pp. 177-185.

Sakoda et al., "Synthesis of 1,4-Dihydropyridine-5-phosphonates and Their Calcium-Antagonistic and Antihypertensive Activites: Novel Calcium-Angatonist 2-[Benzyl(phenyl)amino]ethyl 5-(5,5-Dimethyl-2-oxo-1,3,2-dioxaphosphorian-2-yl)-1,4-dihydro-2,6-dimethyl-4-(3-nitrophenyl)-3-pyridinecarboxylate Hydrochloride Ethanol (NZ-105) and Its Crystal Structure," Chem. Pharm. Bull., vol. 40, No. 9, pp. 2362-2369, 1992.

Sakoda et al., "Synthesis and Biological Activities of Optical Isomers of 2-(4-Diphenylmethyl-1-piperazinyl)ethyl 5-(4,6-Dimethyl-2-oxo-1,3,2-dioxaphosphorinan-2-yl)-1,4-dihydro-2,6-dimethyl-4-(3-nitrophenyl)-3-pyridinecarboxylate Dihydrochloride (NIP-101)," Chem. Pharm. Bull., vol. 40, No. 9, pp. 2370-2376, 1992.

Sugano et al., "T-type calcium channel blockade as a therapeutic strategy against renal injury in rats with subtotal nephrectomy," Kidney International, vol. 73, pp. 826-834, 2008.

Imagawa et al., "Inhibitory Effect of Efonidipine on Aldosterone Synthesis and Secretion in Human Adrenocarcinoma (H295R) Cells," Cardiovasc Pharmacol, vol. 47, No. 1, pp. 133-138, Jan. 2006.

* cited by examiner

T-TYPE CALCIUM CHANNEL BLOCKER

TECHNICAL FIELD

The present invention relates to T-type calcium channel blockers being optically active dihydropyridine-5-phosphonate derivatives in which the absolute configuration of 4-position on dihydropyridine ring is R-configuration. In addition, the present invention relates to therapeutic or preventive agents against diseases for which T-type calcium channel blockers are effective.

BACKGROUND ART

It is known that dihydropyridine-5-phosphonate derivatives (racemate) show oral anti-hypertensive action to be effective for cardiovascular diseases such as angia pectoris, cerebrovascular disease, hypertension or the like (see, for example Patent Documents 1-7).

The above-mentioned effect is owing to vasodilation mainly based on L-type calcium channel blocking action, and similar to that of L-type calcium antagonists represented by other numeral 1,4-dihydropyridine derivatives.

Recently, it was found that efonidipine (racemate) being a representative compound of dihydropyridine-5-phosphonate derivatives has T-type calcium channel blocking action in addition to L-type calcium channel blocking action (see, for example, Non-patent Document 1).

It is reported that the activation of T-type calcium channel participates in occurrence of hypercardia (see, for example Non-patent Document 2), heart failure (see, for example Non-patent Document 2), cardiomyopathy (see, for example Non-patent Document 3), tachyarrhythmia represented by atrial fibrillation (see, for example Non-patent Document 4), arterial sclerosis (see, for example Non-patent Document 5), renal disorder represented by nephritis/nephropathy (see, for example Non-patent Document 6), renal insufficiency (see, for example Non-patent Document 6), inflammation and edema (see, for example Non-patent Document 7), hyperaldosteronism (see, for example Non-patent Document 8), neurogenic pain (see, for example Non-patent Document 9), and epilepsy (see, for example Non-patent Document 10). Therefore, it is though that T-type calcium channel blockers are effective for therapy or prevention of these diseases.

Patent Document 1: JP 61-30591 A (1986)
Patent Document 2: JP 60-69089 A (1985)
Patent Document 3: JP 1-275591 A (1989)
Patent Document 4: JP 61-63688 A (1986)
Patent Document 5: JP 63-233992 A (1988)
Patent Document 6: JP 62-169795 A (1987)
Patent Document 7: JP 62-169796 A (1987)
Non-patent Document 1: Masumiya H et al.: Eur J Pharmacol 335,p. 15-21 (1997)
Non-patent Document 2: Mulder P et al.: J Am Coll Cardiol 29, p. 416-421 (1997)
Non-patent Document 3: Villame J et al.: Cardiovasc Drugs Ther 15, p. 41-48 (2001)
Non-patent Document 4: Fareh S et al.: Circulation 100, p. 2191-2197 (1999)
Non-patent Document 5: Noll G and LuscherTF: Cardiology 89, p. 10-15 (1998)
Non-patent Document 6: Baylis C et al.: Am J Kidney Dis 38 p. 1292-1297 (2001)
Non-patent Document 7: Bilici D et al.: Pharmacol Res 44, p. 527-531 (2001)
Non-patent Document 8: Lenglet S et al.: Endocrinology 143, p. 1748-60 (2002)
Non-patent Document 9: McCallum J B et al.: Anesthesiology 98, p. 209-216 (2003)
Non-patent Document 10: Porcello D M et al.: J Neurophysiol 89, p. 177-185 (2003)

However, dihydropyridine-5-phosphonate derivatives represented by efonidipine (racemate) have a possibility that the influence thereby on vasodilation and cardiac function based on L-type calcium channel blocking action becomes hindrance factors in the therapy of the above-mentioned diseases. In addition, they are liable to cause lowering in Quality of Life, such as headache, flash, dizziness, edema or the like based on vasodilation.

From the above, it is considered very useful to find T-type calcium channel blockers having a weak or little L-type calcium channel blocking action.

The present inventors eagerly investigated in order to solve the above-mentioned problems. As a result of it, they found that optically active dihydropyridine-5-phosphonate derivatives in which the absolute configuration of 4-position on dihydropyridine ring is R-configuration show a weak or little L-type calcium channel blocking action, and a selective blocking action against T-type calcium channel, and they completed the present invention.

DISCLOSURE OF INVENTION

That is, the present invention provides the followings:

1. A T-type calcium channel blocker that is optically active 1,4-dihydropyridine compound, a pharmaceutically acceptable salt thereof or a solvate thereof, of formula (1)

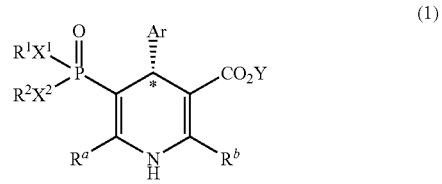

[wherein $R^1$ and $R^2$ are independently of each other $C_{1-6}$ alkyl group {the $C_{1-6}$ alkyl group may be substituted with phenyl group (the phenyl group may be substituted with $C_{1-6}$ alkoxy group or halogen atom), $C_{2-6}$ alkenyl group or $C_{2-6}$ alkynyl group (the $C_{2-6}$ alkenyl group and $C_{2-6}$ alkynyl group may be substituted with phenyl group (the phenyl group may be substituted with $C_{1-6}$ alkoxy group or halogen atom))}, or —$L^1$— $NR^3R^4$ {$R^3$ and $R^4$ are independently of each other $C_{1-6}$ alkyl group (the $C_{1-6}$ alkyl group may be substituted with phenyl group (the phenyl group may be substituted with $C_{1-6}$ alkoxy group or halogen atom)) or phenyl group (wherein the phenyl group may be substituted with $C_{1-6}$ alkoxy group or halogen atom), $L^1$ is $C_{2-6}$ alkylene group (the $C_{2-6}$ alkylene group may be substituted with $C_{1-3}$ alkyl group or phenyl group (the phenyl group may be arbitrarily substituted with halogen atom, $C_{1-3}$ alkyl group or $C_{1-3}$ alkoxy group))}, or $R^1$ and $R^2$ together form —$CR^5R^6$—$CR^7R^8$—, —$CR^5R^6$— $CR^7R^8$—$CR^9R^{10}$— or —$CR^5R^6$—$CR^7R^8$—$CR^9R^{10}$— $CR^{11}R^{12}$— ($R^5$ to $R^{12}$ are independently of each other hydrogen atom or $C_{1-6}$ alkyl group, or any two of them together with the carbon atom bonding them may form 5-, 6- or 7-membered ring);

$X^1$ and $X^2$ are independently of each other O or $NR^{13}$ ($R^{13}$ is hydrogen atom or $C_{1-6}$ alkyl group);

Ar is phenyl group, pyridyl group, furyl group or 2,1,3-benzoxadiazol-4-yl group {the phenyl group, pyridyl group, furyl group and 2,1,3-benzoxadiazol-4-yl group may arbitrarily substituted with one or two substituents selected from $NO_2$, $CF_3$, Br, Cl, F, R(R is $C_{1-20}$ alkyl group), OH, $OR^{14}$ ($R^{14}$ is $C_{1-6}$ alkyl group), $OCHF_2$, $COOR^{14}$, $NH_2$, $NHR^{14}$, $NR^{14}R^{15}$ ($R^{15}$ is $C_{1-6}$ alkyl group), $CONH_2$, $CONHR^{14}$, $CONR^{14}R^{15}$, $COSR^{14}$, $SR^{14}$, $S(O)R^{14}$, $S(O)_2R^{14}$, $SO_3H$, $SO_3R^{14}$, $SO_2NH_2$, $SO_2NHR^{14}$, $SO_2NR^{14}R^{15}$, CN and phenyloxy group};

$R^a$ and $R^b$ are independently of each other $C_{1-6}$ alkyl group, $-L^2-NR^{16}R^{17}$ {$R^{16}$ and $R^{17}$ are independently of each other hydrogen atom, $C_{1-6}$ alkyl group (the $C_{1-6}$ alkyl group may be substituted with phenyl group (the phenyl group may be substituted with $C_{1-6}$ alkoxy group or halogen atom)) or phenyl group (the phenyl group may be substituted with $C_{1-6}$ alkoxy group or halogen atom), $L^2$ is $C_{2-6}$ alkylene group (the $C_{2-6}$ alkylene group may be arbitrarily substituted with $C_{1-3}$ alkyl group or phenyl group (the phenyl group may be arbitrarily substituted with halogen atom, $C_{1-3}$ alkyl group or $C_{1-3}$ alkoxy group))}, $CH_2O-L^2-NR^{16}R^{17}$, $Ar_1$ ($Ar_1$ is phenyl group (the phenyl group may be arbitrarily substituted with halogen atom, $C_{1-3}$ alkyl group or $C_{1-3}$ alkoxy group)), $CH=CHAr_1$, $CH_2CH(OH)Ar_1$, CHO, CN, $CH_2OH$, $CHOR^{16}$, $-L^2-N(CH_2CH_2)_2NR^{16}$ or $NR^{16}R^{17}$;

Y is $C_{1-20}$ alkyl group {the $C_{1-20}$ alkyl group may be substituted with phenyl group (the phenyl group may be substituted with $C_{1-6}$ alkoxy group or halogen atom), $C_{2-6}$ alkenyl group or $C_{2-6}$ alkynyl group (the $C_{2-6}$ alkenyl group and $C_{2-6}$ alkynyl group may be substituted with phenyl group (the phenyl group may be substituted with $C_{1-6}$ alkoxy group or halogen atom))}, $-L^3-NR^{16}R^{19}$ {$R^{18}$ and $R^{19}$ are independently of each other $C_{1-6}$ alkyl group (the $C_{1-6}$ alkyl group may be substituted with phenyl group (the phenyl group may be substituted with $C_{1-6}$ alkoxy group or halogen atom)) or phenyl group (the phenyl group may be substituted with $C_{1-6}$ alkoxy group or halogen atom), $L^3$ is $C_{2-6}$ alkylene group (the $C_{2-6}$ alkylene group may be arbitrarily substituted with $C_{1-3}$ alkyl group or phenyl group (the phenyl group may be arbitrarily substituted with halogen atom, $C_{1-3}$ alkyl group or $C_{1-3}$ alkoxy group))},

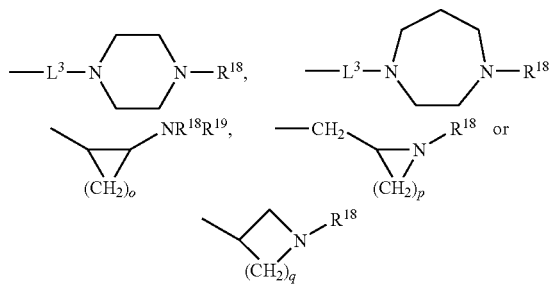

(wherein o and p are independently of each other 3 or 4, q is 1, 2 or 3), and * is absolute configuration of R.].

2. The T-type calcium channel blocker that is optically active 1,4-dihydropyridine compound, a pharmaceutically acceptable salt thereof or a solvate thereof, as set forth in 1., wherein Y is $-L^3-NR^{18}R^{19}$ {$R^{18}$ and $R^{19}$ are independently of each other $C_{1-6}$ alkyl group (the $C_{1-6}$ alkyl group may be substituted with phenyl group (the phenyl group may be substituted with $C_{1-6}$ alkoxy group or halogen atom)) or phenyl group (the phenyl group may be substituted with $C_{1-6}$ alkoxy group or halogen atom), $L^3$ is $C_{2-6}$ alkylene group (the $C_{2-6}$ alkylene group may be arbitrarily substituted with $C_{1-3}$ alkyl group or phenyl group (the phenyl group may be arbitrarily substituted with halogen atom, $C_{1-3}$ alkyl group or $C_{1-3}$ alkoxy group))},

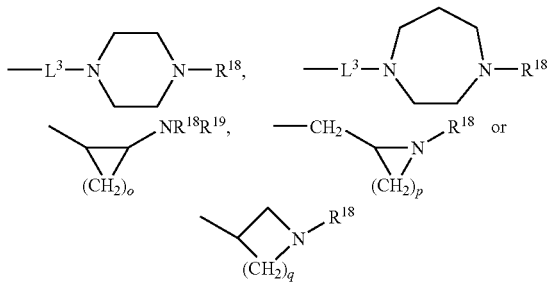

(wherein o and p are independently of each other 3 or 4, q is 1, 2 or 3), and $R^a$ is $C_{1-6}$ alkyl group;

3. The T-type calcium channel blocker that is optically active 1,4-dihydropyridine compound, a pharmaceutically acceptable salt thereof or a solvate thereof, as set forth in 2., wherein $R^b$ is $C_{1-6}$ alkyl group, CN or $NH_2$;

4. The T-type calcium channel blocker that is optically active 1,4-dihydropyridine compound, a pharmaceutically acceptable salt thereof or a solvate thereof, as set forth in 1., wherein Y is $C_{1-20}$ alkyl group {the $C_{1-20}$ alkyl group may be substituted with phenyl group (the phenyl group may be substituted with $C_{1-6}$ alkoxy group or halogen atom), $C_{2-6}$ alkenyl group or $C_{2-6}$ alkynyl group (the $C_{2-6}$ alkenyl group and $C_{2-6}$ alkynyl group may be substituted with phenyl group (the phenyl group may be substituted with $C_{1-6}$ alkoxy group or halogen atom))}, $R^b$ is $-L^2-NR^{16}R^{17}$ {$R^{16}$ and $R^{17}$ are independently of each other hydrogen atom, $C_{1-6}$ alkyl group (the $C_{1-6}$ alkyl group may be substituted with phenyl group (the phenyl group may be substituted with $C_{1-6}$ alkoxy group or halogen atom)) or phenyl group (the phenyl group may be substituted with $C_{1-6}$ alkoxy group or halogen atom), $L^2$ is $C_{2-6}$ alkylene group (the $C_{2-6}$ alkylene group may be arbitrarily substituted with $C_{1-3}$ alkyl group or phenyl group (the phenyl group may be arbitrarily substituted with halogen atom, $C_{1-3}$ alkyl group or $C_{1-3}$ alkoxy group))}, $CH_2O-L^2-NR^{16}R^{17}$ or $-L^2-N(CH_2CH_2)_2NR^{16}$, and $R^a$ is $C_{1-6}$ alkyl group;

5. The T-type calcium channel blocker that is optically active 1,4-dihydropyridine compound, a pharmaceutically acceptable salt thereof or a solvate thereof, as set forth in 2., 3. or 4., wherein $R^1$ and $R^2$ are independently of each other $C_{1-6}$ alkyl group {the $C_{1-6}$ alkyl group may be substituted with phenyl group (the phenyl group may be substituted with $C_{1-6}$ alkoxy group or halogen atom), $C_{2-6}$ alkenyl group or $C_{2-6}$ alkynyl group (the $C_{2-6}$ alkenyl group and $C_{2-6}$ alkynyl group may be substituted with phenyl group (the phenyl group may be substituted with $C_{1-6}$ alkoxy group or halogen atom))}, or $R^1$ and $R^2$ together form $-CR^5R^6-CR^7R^8-$, $-CR^5R^6-CR^7R^8-CR^9R^{10}-$ or $-CR^5R^6-CR^7R^8-CR^9R^{10}-CR^{11}R^{12}-$ ($R^5$ to $R^{12}$ are independently of each other hydrogen atom or $C_{1-6}$ alkyl group, or any two of them together with the carbon atom bonding them may form 5,6- or 7-membered ring);

$X^1$ and $X^2$ are both O;

6. The T-type calcium channel blocker that is optically active 1,4-dihydropyridine compound, a pharmaceutically acceptable salt thereof or a solvate thereof, as set forth in 5., wherein Ar is phenyl, 3-nitrophenyl, 2-nitrophenyl, 3-chlorophenyl, 2-chlorophenyl, 3-methoxyphenyl, 2-methoxyphenyl, 2-trifluoromethylphenyl, 24rifluoromethylphenyl or 2,3-dichlorophenyl;

7. The T-type calcium channel blocker that is optically active 1,4-dihydropyridine compound, a pharmaceutically acceptable salt thereof or a solvate thereof, as set forth in 6., wherein $R^1$ and $R^2$ together form —$CH_2$—$C(CH_3)_2$—$CH_2$—, $X^1$ and $X^2$ are both 0, Ar is 3-nitrophenyl, $R^a$ and $R^b$ are both methyl, and Y is 2-[benzyl(phenyl)amino]ethyl;

8. A pharmaceutical containing the T-type calcium channel blocker as set forth in any one of 1. to 7.;

9. A therapeutic or preventive agent against a disease for which T-type calcium channel blocking action is effective, containing the T-type calcium channel blocker as set forth in any one of 1. to 7.;

10. A therapeutic or preventive agent against hypercardia, containing the T-type calcium channel blocker as set forth in any one of 1. to 7.;

11. A therapeutic or preventive agent against heart failure, containing the T-type calcium channel blocker as set forth in any one of 1. to 7.;

12. A therapeutic or preventive agent against cardiomyopathy, containing the T-type calcium channel blocker as set forth in any one of 1. to 7.;

13. A therapeutic or preventive agent against atrial fibrillation, containing the T-type calcium channel blocker as set forth in any one of 1. to 7.;

14. A therapeutic or preventive agent against tachycardia-arrhythmia, containing the T-type calcium channel blocker as set forth in any one of 1. to 7.;

15. A therapeutic or preventive agent against arterial sclerosis, containing the T-type calcium channel blocker as set forth in any one of 1. to 7.;

16. A therapeutic or preventive agent against nephritis, containing the T-type calcium channel blocker as set forth in any one of 1. to 7.;

17. A therapeutic or preventive agent against nephropathy, containing the T-type calcium channel blocker as set forth in any one of 1. to 7.;

18. A therapeutic or preventive agent against renal disorder, containing the T-type calcium channel blocker as set forth in any one of 1. to 7.;

19. A therapeutic or preventive agent against renal insufficiency, containing the T-type calcium channel blocker as set forth in any one of 1. to 7.;

20. A therapeutic or preventive agent against edema, containing the T-type calcium channel blocker as set forth in any one of 1. to 7.;

21. A therapeutic or preventive agent against inflammation, containing the T-type calcium channel blocker as set forth in any one of 1. to 7.;

22. A therapeutic or preventive agent against hyper-aldosteronism, containing the T-type calcium channel blocker as set forth in any one of 1. to 7.;

23. A therapeutic or preventive agent against neurogenic pain, containing the T-type calcium channel blocker as set forth in any one of 1. to 7.; and 24. A therapeutic or preventive agent against epilepsy, containing the T-type calcium channel blocker as set forth in any one of 1. to 7.

BEST MODE FOR CARRYING OUT THE INVENTION

Hereinafter, the present invention is described in further detail.

In the meantime, "n" means normal, "i" means iso, "s" means secondary, "t" means tertiary and "c" means cyclo in this specification.

Each substituent stated in this specification is described.

Halogen atom includes fluorine atom, chlorine atom, bromine atom and iodine atom.

$C_{1-3}$ alkyl group may be a straight-chain alkyl group, branched alkyl group or $C_3$ cycloalkyl group, and includes for example methyl group, ethyl group, n-propyl group, i-propyl group and c-propyl group, etc.

$C_{1-6}$ alkyl group may be a straight-chain alkyl group, branched alkyl group or $C_{3-6}$ cycloalkyl group, and includes for example in addition to the above-mentioned substituents for $C_{1-3}$ alkyl group, n-butyl group, i-butyl group, s-butyl group, t-butyl group, c-butyl group, n-pentyl group, 1-methyl-n-butyl group, 2-methyl-n-butyl group, 3-methyl-n-butyl group, 1,1-dimethyl-n-propyl group, c-pentyl group, 2-methyl-c-butyl group, n-hexyl group, 1-methyl-n-pentyl group, 2-methyl-n-pentyl group, 1,1-dimethyl-n-butyl group, 1-ethyl-n-butyl group, 1,1,2-trimethyl-n-propyl group, c-hexyl group, 1-methyl-c-pentyl group, 1-ethyl-c-butyl group and 1,2-dimethyl-c-butyl group, etc.

$C_{1-20}$ alkyl group may be a straight-chain alkyl group, branched alkyl group or $C_{3-20}$ cycloalkyl group, and includes for example in addition to the above-mentioned substituents for $C_{1-6}$ alkyl group, n-heptyl group, 2-c-pentylethyl group, n-octyl group, 2-c-hexylethyl group, 3-c-pentyl-n-propyl group, n-nonyl group, 3-c-hexyl-n-propyl group, 4-c-pentyl-n-butyl group, n-decyl group, 4-c-hexyl-n-butyl group, 5-c-pentyl-n-pentyl group, n-undecyl group, 5-c-hexyl-n-pentyl group, 6-c-pentyl-n-hexyl group, n-dodecyl group, n-tridecyl group, n-tetradecyl group, n-pentadecyl group, n-hexadecyl group, n-heptadecyl group, n-octadecyl group, n-nonadecyl group and n-eicosyl, etc.

$C_{2-6}$ alkenyl group includes straight-chain or branched ones, and ethenyl group, 1-propenyl group, 2-propenyl group, 1-methyl-1-ethenyl group, 1-butenyl group, 2-butenyl group, 3-butenyl group, 2-methyl-1-propenyl group, 2-methyl-2-propenyl group, 1-ethylethenyl group, 1-methyl-1-propenyl group, 1-methyl-2-propenyl group, 1-pentenyl group, 2-pentenyl group, 3-pentenyl group, 4-pentenyl group, 1-n-propylethenyl group, 1-methyl-1-butenyl group, 1-methyl-2-butenyl group, 1-methyl-3-butenyl group, 2-ethyl-2-propenyl group, 2-methyl-1-butenyl group, 2-methyl-2-butenyl group, 2-methyl-3-butenyl group, 3-methyl-1-butenyl group, 3-methyl-2-butenyl group, 3-methyl-3-butenyl group, 1,1-dimethyl-2-propenyl group, 1-1-propylethenyl group, 1,2-dimethyl-1-propenyl group, 1,2-dimethyl-2-propenyl group, 1-hexenyl group, 2-hexenyl group, 3-hexenyl group, 4-hexenyl group, 5-hexenyl group, 1-methyl-1-pentenyl group, 1-methyl-2-pentenyl group, 1-methyl-3-pentenyl group, 1-methyl-4-pentenyl group, 1-n-butylethenyl group, 2-methyl-1-pentenyl group, 2-methyl-2-pentenyl group, 2-methyl-3-pentenyl group, 2-methyl-4-pentenyl group, 2-n-propyl-2-propenyl group, 3-methyl-1-pentenyl group, 3-methyl-2-pentenyl group, 3-methyl-3-pentenyl group, 3-methyl-4-pentenyl group, 3-ethyl-3-butenyl group, 4-methyl-1-pentenyl group, 4-methyl-2-pentenyl group, 4-methyl-3-pentenyl group, 4-methyl-4-pentenyl group, 1,1-dimethyl-2-butenyl group, 1,1-dimethyl-3-butenyl group, 1,2-dimethyl-1-butenyl group, 1,2-dimethyl-2-butenyl group, 1,2-dimethyl-3-butenyl group, 1-methyl-2-ethyl-2-propenyl group, 1-s-butylethenyl group, 1,3-dimethyl-1-butenyl group, 1,3-dimethyl-2-butenyl group, 1,3-dimethyl-3-butenyl group, 1-1-butylethenyl group, 2,2-dimethyl-3-butenyl group, 2,3-dimethyl-1-butenyl group, 2,3-dimethyl-2-butenyl group, 2,3-dimethyl-3-butenyl group, 2-1-propyl-2-propenyl group, 3,3-dimethyl-1-butenyl group, 1-ethyl-1-butenyl group, 1-ethyl-2-butenyl group, 1-ethyl-3-butenyl group, 1-n-propyl-1-propenyl group, 1-n-propyl-2-propenyl group, 2-ethyl-1-butenyl group, 2-ethyl-2-butenyl group, 2-ethyl-3-butenyl group, 1,1,2-trimethyl-2-propenyl group, 14-butylethenyl group, 1-methyl-1-ethyl-2-propenyl group, 1-ethyl-2-methyl-1-propenyl group, 1-ethyl-2-methyl-2-propenyl group, 1-1-propyl-1-propenyl group and 1-1-propyl-2-propenyl group, etc.

$C_{2-6}$ alkynyl group includes straight-chain or branched ones, and ethynyl group, 1-propynyl group, 2-propynyl group, 1-butynyl group, 2-butynyl group, 3-butynyl group, 1-methyl-2-propynyl group, 1-pentynyl group, 2-pentynyl group, 3-pentynyl group, 4-pentynyl group, 1-methyl-2-butynyl group, 1-methyl-3-butynyl group, 2-methyl-3-butynyl group, 3-methyl-1-butynyl group, 1,1-dimethyl-2-propynyl group, 2-ethyl-2-propynyl group, 1-hexynyl group, 2-hexynyl group, 3-hexynyl group, 4-hexynyl group, 5-hexynyl group, 1-methyl-2-pentynyl group, 1-methyl-3-pentynyl group, 1-methyl-4-pentynyl group, 2-methyl-3-pentynyl group, 2-methyl-4-pentynyl group, 3-methyl-1-pentynyl group, 3-methyl-4-pentynyl group, 4-methyl-1-pentynyl group, 4-methyl-2-pentynyl group, 1,1-dimethyl-2-butynyl group, 1,1-dimethyl-3-butynyl group, 1,2-dimethyl-3-butynyl group, 2,2-dimethyl-3-butynyl group, 3,3-dimethyl-1-butynyl group, 1-ethyl-2-butynyl group, 1-ethyl-3-butynyl group, 1-n-propyl-2-propynyl group, 2-ethyl-3-butynyl group, 1-methyl-1-ethyl-2-propynyl group and 1-1-propyl-2-propynyl group, etc.

$C_{1-3}$ alkoxy group may be a straight-chain alkoxy group, branched alkoxy group or $C_3$ cycloalkoxy group, and includes for example methoxy group, ethoxy group, n-propoxy group, i-propoxy group and c-propoxy group, etc.

$C_{1-6}$ alkoxy group may be a straight-chain alkoxy group, branched alkoxy group or $C_{3-6}$ cycloalkoxy group, and includes for example in addition to the above-mentioned substituents for $C_{1-3}$ alkoxy group, n-butoxy group, i-butoxy group, s-butoxy group, t-butoxy group, c-butoxy group, n-pentyloxy group, 1-methyl-n-butoxy group, 2-methyl-n-butoxy group, 3-methyl-n-butoxy group, 1,1-dimethyl-n-propoxy group, c-pentyloxy group, 2-methyl-c-butoxy group, n-hexyloxy group, 1-methyl-n-pentyloxy group, 2-methyl-n-pentyloxy group, 1,1-dimethyl-n-butoxy group, 1-ethyl-n-butoxy group, 1,1,2-trimethyl-n-propoxy group, c-hexyloxy group, 1-methyl-c-pentyloxy group, 1-ethyl-c-butoxy group and 1,2-dimethyl-c-butoxy group, etc.

$C_{2-6}$ alkylene group includes ethylene group, propylene group, butylene group, pentylene group and hexylene group, etc.

5-, 6- or 7-membered rings include c-pentyl, c-hexyl and c-heptyl, etc.

Preferable $R^1$ and $R^2$ include the followings in which the latter is more preferable:

1. $R^1$ and $R^2$ together form $-CR^5R^6-CR^7R^8-$, $-CR^5R^6-CR^7R^8-CR^9R^{10}-$ or $-CR^5R^6-CR^7R^8-CR^9R^{10}-CR^{11}R^{12}-$ ($R^5$ to $R^{12}$ are independently of each other hydrogen atom or $C_{1-6}$ alkyl group, or any two of them together with the carbon atom bonding them may form 5-, 6- or 7-membered ring);

2. $R^1$ and $R^2$ together form $-CR^5R^6-CR^7R^8-CR^9R^{10}-$ ($R^5$ to $R^{10}$ are independently of each other hydrogen atom or $C_{1-6}$ alkyl group);

3. $R^1$ and $R^2$ together form $-CH_2-C(CH_3)_2-CH_2-$ or $-CHCH_3-CH_2-CHCH_3-$;

4. $R^1$ and $R^2$ are independently of each other $C_{1-6}$ alkyl group {the $C_{1-6}$ alkyl group may be substituted with phenyl group (the phenyl group may be substituted with $C_{1-6}$ alkoxy group or halogen atom), $C_{2-6}$ alkenyl group or $C_{2-6}$ alkynyl group (the $C_{2-6}$ alkenyl group and $C_{2-6}$ alkynyl group may be substituted with phenyl group (the phenyl group may be substituted with $C_{1-6}$ alkoxy group or halogen atom))};

5. $R^1$ and $R^2$ are independently of each other $C_{1-6}$ alkyl group;

6. $R^1$ and $R^2$ are both methyl group.

Preferable $X^1$ and $X^2$ include the followings in which the latter is more preferable:

1. $X^1$ and $X^2$ are both O.

Preferable Ar includes the followings:

1. Phenyl group, 4-nitrophenyl group, 3-nitrophenyl group, 2-nitrophenyl group, 4-chlorophenyl group, 3-chlorophenyl group, 2-chlorophenyl group, 4-methoxyphenyl group, 3-methoxyphenyl group, 2-methoxyphenyl group, 4-trifluoromethylphenyl group, 3-trifluoromethylphenyl group, 2-trifluoromethylphenyl group and 2,3-dichlorophenyl group;

2. Phenyl group, 3-nitrophenyl group, 2-nitrophenyl group, 3-chlorophenyl group, 2-chlorophenyl group, 3-methoxyphenyl group, 2-methoxyphenyl group, 3-trifluoromethylphenyl group, 2-trifluoromethylphenyl group and 2,3-dichlorophenyl group;

3. Phenyl group, 3-nitrophenyl group, 2-nitrophenyl group, 3-chlorophenyl group, 2-chlorophenyl group, 3-methoxyphenyl group, 2-methoxyphenyl group, 3-trifluoromethylphenyl group and 2-trifluoromethylphenyl group;

4. Phenyl group, 3-nitrophenyl group, 2-nitrophenyl group, 3-methoxyphenyl group, 2-methoxyphenyl group, 3-trifluoromethylphenyl group and 2-trifluoromethylphenyl group.

Preferable $R^a$ includes the followings:

1. $C_{1-6}$ alkyl group; more preferably

2. Methyl group.

Preferable $R^b$ includes the followings in which the latter is more preferable:

1. $C_{1-6}$ alkyl group, CN and $NH_2$;

2. Methyl group, CN and $NH_2$;

3. $-L^2-NR^{16}R^{17}$ {$R^{16}$ and $R^{17}$ are independently of each other hydrogen atom, $C_{1-6}$ alkyl group (the $C_1$ alkyl group may be substituted with phenyl group (the phenyl group may be substituted with $C_{1-6}$ alkoxy group or halogen atom)) or phenyl group (the phenyl group may be substituted with $C_{1-6}$ alkoxy group or halogen atom), $L^2$ is $C_{2-6}$ alkylene group (the $C_{2-6}$ alkylene group may be arbitrarily substituted with $C_{1-3}$ alkyl group or phenyl group (the phenyl group may be arbitrarily substituted with halogen atom, $C_{1-3}$ alkyl group or $C_{1-3}$ alkoxy group))), —$CH_2O$—$L^2$—$NR^{16}R^{17}$ and —$L^2$—$N(CH_2CH_2)_2NR^{16}$;

4. —$CH_2O$—$L^2$—$NR^{16}R^{17}$;

5. —$CH_2OCH_2CH_2NH_2$.

Preferable Y includes the followings in which the latter is more preferable:

1. $C_{1-20}$ alkyl group {the $C_{1-20}$ alkyl group may be substituted with phenyl group (the phenyl group may be substituted with $C_{1-6}$ alkoxy group or halogen atom), $C_{2-6}$ alkenyl group or $C_{2-6}$ alkynyl group (the $C_{2-6}$ alkenyl group and $C_{2-6}$ alkynyl group may be substituted with phenyl group (the phenyl group may be substituted with $C_{1-6}$ alkoxy group or halogen atom))};

2. Methyl group, ethyl group, i-propyl group, i-butyl group and methoxyethyl group;

3. —$L^3$—$NR^{18}R^{19}$ {$R^{18}$ and $R^{19}$ are independently of each other $C_{1-6}$ alkyl group (the $C_{1-6}$ alkyl group may be substituted with phenyl group (the phenyl group may be substituted with $C_{1-6}$ alkoxy group or halogen atom)) or phenyl group (the phenyl group may be substituted with $C_{1-4}$ alkoxy group or halogen atom), $L^3$ is $C_{2-6}$ alkylene group (the $C_{2-6}$ alkylene group may be arbitrarily substituted with $C_{1-3}$ alkyl group or phenyl group (the phenyl group may be arbitrarily substituted with halogen atom, $C_{1-3}$ alkyl group or $C_{1-3}$ alkoxy group))},

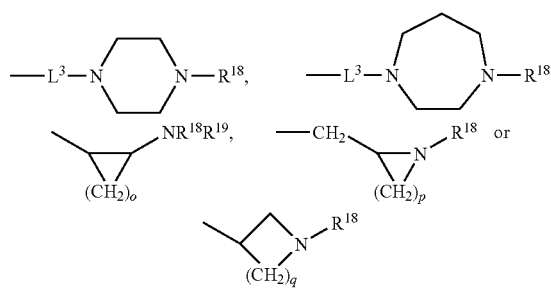

(wherein o and p are independently of each other 3 or 4, q is 1, 2 or 3);

4.

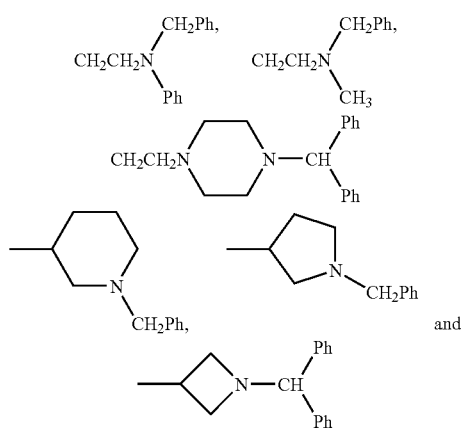

When the optically active 1,4-dihydropyridine compound used in the present invention is a compound that can form a salt, the pharmaceutically acceptable salt thereof can be also used as an effective component.

The pharmaceutically acceptable salt includes hydrochlorides, hydrobromides, sulfates, methanesulfonates, acetates, benzoates, tartrates, phosphates, lactates, maleates, fumarates, malates, gluconates, salicylates and the like.

Preferably, hydrochlorides and methanesulfonates may be mentioned.

The solvates are not specifically limited so long as they are pharmaceutically acceptable, and concretely include hydrates and a solvate with ethanol, and the like.

T-type calcium channel blockers that are optically active 1,4-dihydropyridine compound, a pharmaceutically acceptable salt thereof or a solvate thereof used in the present invention, pharmaceuticals containing the T-type calcium channel blockers, or therapeutic agents against diseases for which T-type calcium channel blocking action is effective, can be generally administered in oral administration forms such as tablets, capsules, powders, granules, pills, syrups and the like, permucosal absorption preparations such as intrarectal administration preparations, transnasal absorption preparations, transvaginal absorption preparations and the like, transpulmonary absorption preparations, inhalants, ophthalmic solutions, percutaneous absorption preparations or injections. The present preparations can be administered as a simple therapeutic agent or as a mixture with other therapeutic agent. They may be administered as a single item but are generally administered in a form of pharmaceutical composition. These preparations can be produced according to any conventional method by adding pharmacologically and pharmaceutically acceptable additives. That is, for oral preparations, additives such as excipients, lubricants, binders, disintegrators, humectants, plasticizers, coating agents and the like can be used. Oral liquids may be in a form of aqueous or oily suspension, solution, emulsion, syrup, elixir and the like, or be provided as a dry syrup that is prepared with water or other appropriate solvent prior to use. The above-mentioned liquids may contain conventional additives such as suspending agents, perfumes, diluents or emusifiers. When it is administered intrarectally, it can be administered as a suppository. The suppository may contain suitable base ingredients such as cocoa fats, lauric fats, macrogol, glycerogelatin, witepsol, sodium stearate or a mixture thereof, and optionally emulsifiers, suspending agents, preservatives and the like. For the injections, the followings are used: resolvents or solubilizing agents, such as distilled water for injections that can constitute aqueous dosage form or on use-dissolved type dosage form, saline, 5% glucose solution, propylene glycol and the like, pharmaceutical ingredients such as pH adjusters, isotonizing agents, stabilizers and the like.

When the pharmaceuticals of the present invention are administered to human, the dosage is determined depending on age or state of the patient. In case where the patient is adult, oral preparations or intrarectal administration is carried out in an amount of about 0.1 mg to 1000 mg per day per body, and an injection is administered in an amount of about 0.05 mg to 500 mg per day per body. These values are merely examples, and the dosage is determined according to the condition of a patient.

The scene which the present invention is applied includes the scene which the use of the compounds having T-type calcium channel blocking activity is expected to improve the condition of the disease. Concretely, the compounds of the present invention are effective for therapy or prevention of hypercardia, heart failure, cardiomyopathy, tachyarrhythmia represented by atrial fibrillation, arterial sclerosis, renal disorder represented by nephritis/nephropathy, renal insufficiency, inflammation and edema, hyper-aldosteronism, neurogenic pain, epilepsy, and the like.

The optically active 1,4-dihydropyridine compounds of formula (I) can be produced with reference to the methods described in JP 1-113398 A (1989), JP 2-011592 A (1990), Chem. Pharm. Bull., 40(9), 2377-2381 (1992) and Chem. Pharm. Bull., 40(9), 2370-2376 (1992).

The production process thereof is shown in Scheme 1.

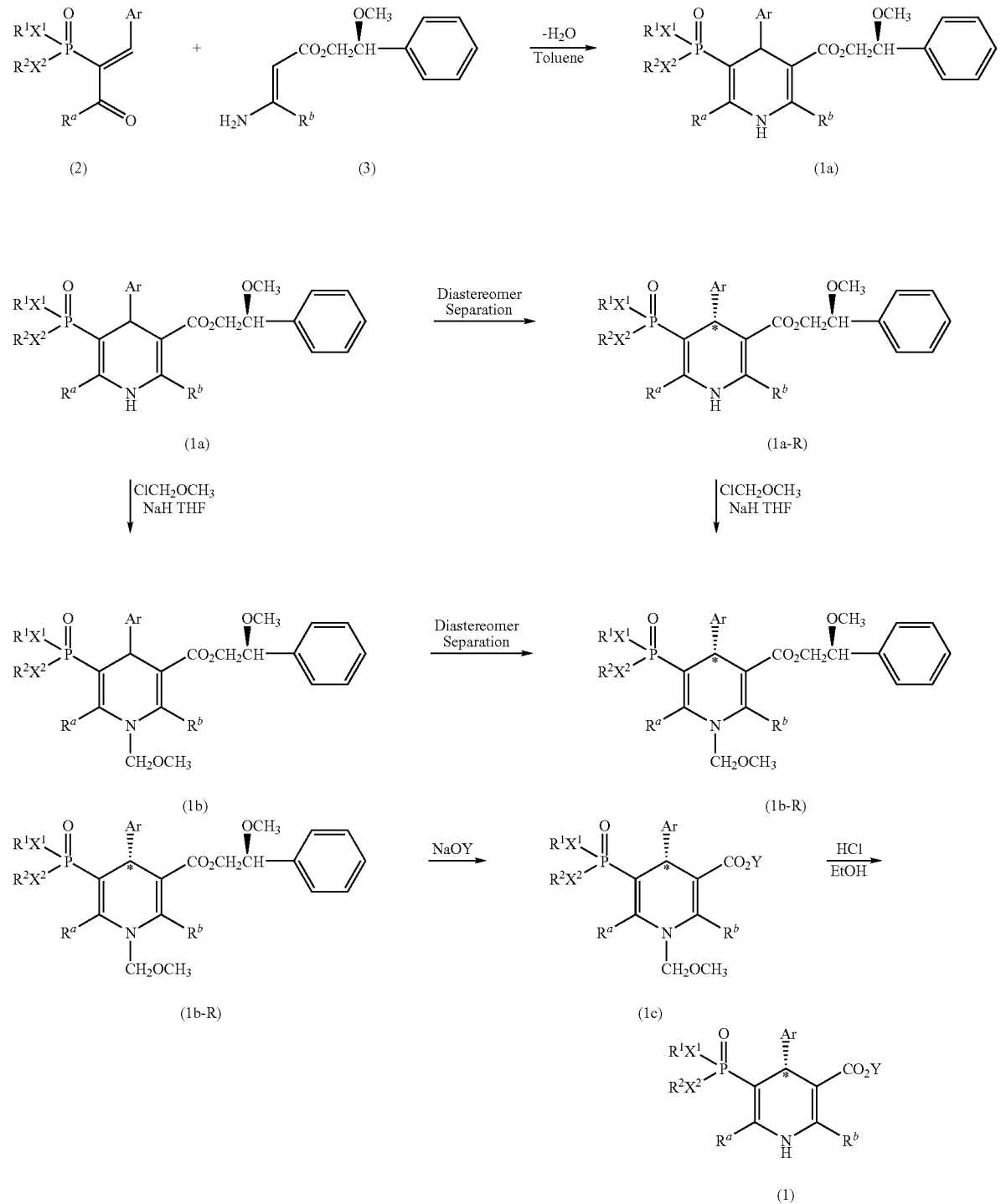

wherein $R^1$, $R^2$, $X^1$, $X^2$, $R^a$, $R^b$, Ar, Y and * are defined similarly to the above.

First of all, styryl phosphonate (2) and optically active aminocrotonic acid derivative (3) are heated in toluene under azeotropic dehydration condition to obtain 1,4-dihydropyridine derivative (1a).

Next, 1,4-dihydropyridine derivative (1a) is subjected to diastereomer separation with crystallization or chromatography, etc. to obtain (1a-R), and then the (1a-R) is subjected to methoxymethylation to obtain (1b-R), or the (1a) is subjected to methoxymethylation to obtain (1b), and then the (1b) is subjected to diastereomer separation with crystallization or chromatography, etc. to obtain (1b-R).

Then, transesterification is carried out and methoxymethyl group is eliminated with hydrogen chloride to produce optically active 1,4-dihydropyridine compound of formula (1).

In addition, according to the methods described in JP 59-161392 A (1984), JP 60-69089 A (1985), JP 60-248693 A (1985), JP 60-258194 A (1985), JP 61-30591 A (1986), JP 61-37793 A (1986), JP 61-63688 A (1986), JP 61-210092 A (1986), JP 61-254569 A (1986), JP 62-169795 A (1987), JP 62-169796 A (1987), JP 62-195392 A (1987), JP 63-68591 A (1988), JP 63-233992 (1988), JP 1-113398 A (1989), JP 1-275591 A (1989), Chem. Pharm. Bull., 40(9), p. 2362-2369, (1992) and Chem. Pharm. Bull., 40(9), p. 2370-2376, (1992), racemic 1,4-dihydropyridine compound is produced, and then optically active 1,4-dihydropyridine compound can be also produced by separating it with HPLC by use of an optically active column.

Hereinafter, the present invention is described based on examples to which the present invention is not limited at all.

Racemic efonidipine synthesized according to the method described in JP 63-233992 A (1988) was collected with HPLC through optically active isomer separation column to obtain R-form and S-form of efonidipine (1,4-dihydro-2,6-dimethyl-5-(5,5-dimethyl-2-oxo-1,3,2-d ioxaphosphorinan-2-yl)-4-(3-ni trophenyl)-3-pyridine carboxylic acid 2-[benzyl (phenyl)amino]ethylester) that was used as examples.

HPLC Collection Condition

Column: CHIRALCEL OC (manufactured by Daicel Chemical Industries, Ltd.)

Column size: 20 cmφ×50 cm

Eluent: methanol

Column temperature: room temperature

Flow rate: 760 mL/min.

In the meantime, compounds as examples other than the above-mentioned efonidipine compound were synthesized as follows:

The compounds that 5-position of dihydropyridine ring is diethylphosphonyl (Z2) were synthesized with reference to the production process described in JP 60-69089 A (1985) and JP 60-248693 A (1985).

The compounds that 5-position of dihydropyridine ring is 5,5-dimethyl-2-oxo-1,3,2-dioxaphosphorinan-2-yl (Z1) were synthesized with reference to the production process described in JP 62-169795 A (1987) and Chem. Pharm. Bull., 40(9), p. 2362-2369 (1992).

The compounds that 5-position of dihydropyridine ring is 4,6-dimethyl-2-oxo-1,3,2-dioxaphosphorinan-2-yl (Z3, Z4) were synthesized with reference to the production process described in JP 63-68591 A (1988) and Chem. Pharm. Bull., 40(9), p. 2370-2376 (1992).

In addition, the following compound (1-a) was produced according to the process shown below.

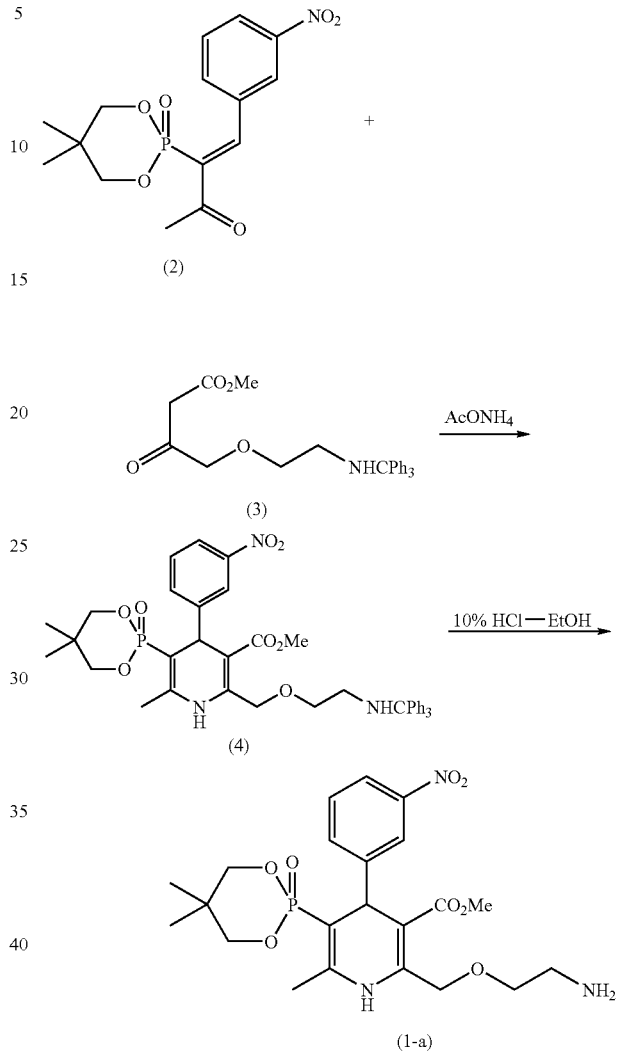

After 8.05 g (19.3 mmol) of compound (3), 1.64 g (21.3 mmol) of ammonium acetate and 80 ml of ethanol were mixed, the resulting mixture was refluxed with heating for 45 minutes. To the obtained reaction solution, 7.23 g (21.3 mmol) of compound (2) was added, and the resulting mixture was further refluxed with heating for 3 hours. After cooling, the solvent was distilled off under a reduced pressure, and 100 ml of toluene and 50 ml of 10% sodium carbonate aqueous solution were added, then the resulting mixture was shaken and allowed to stand and thereby separated into phases. The organic phase was washed with 20% sodium chloride solution, dried over magnesium sulfate (anhydrous), and then the solvent was distilled off under a reduced pressure. The residue was purified with silica gel chromatography (hexane-ethyl acetate 4:1, V/V to ethyl acetate) to obtain 6.04 g (yield 42%) of compound (4) as yellow amorphous.

(Compound (3) was produced according to the method described in EP0599220A1.) MS m/z: 738 ($M^+$+1), $^1$H-NMR (CDCl$_3$) δ (ppm): 0.87 (3H, s), 1.08 (3H, s), 2.39 (3H, d), 2.42

(2H, t), 3.51-3.73 (4H, m), 3.69 (3H, s), 4.21-4.31 (2H, m), 4.56 (1H, d), 4.70 (1H, d), 4.93 (1H, d), 7.17-7.49 (16H, m), 7.62 (1H, d), 8.02 (1H, d), 8.11 (1H, m).

After 500 mg (0.678 mmol) of compound (4) was dissolved in 5 ml of methanol, 500 mg (1.37 mmol) of 10% HCl-MeOH was added thereto and the resulting mixture was refluxed with heating for 2.5 hours. After cooling on standing, the solvent was distilled off under a reduced pressure, and 20 ml of chloroform and 10 ml of 10% sodium carbonate aqueous solution were added, then the resulting mixture was shaken and allowed to stand and thereby separated into phases. The organic phase was washed with water, dried over magnesium sulfate (anhydrous), and then the solvent was distilled off under a reduced pressure. The residue was purified with silica gel chromatography (hexane-ethyl acetate 20:1 to ethyl acetate, then chloroform-methanol 5:1, V/V) to obtain 216 mg (yield 64%) of compound (1-a) as yellow oily product.

MS m/z: 495 (M$^+$), $^1$H-NMR (CDCl$_3$) δ (ppm): 0.89 (3H, s), 1.04 (3H, s), 2.46 (3H, d), 3.00-3.03 (2H, m), 3.54-3.74 (4H, m), 3.68 (3H, s), 4.09-4.27 (2H, m), 4.61 (1H, d), 4.66 (1H, d), 4.89 (1H, d), 7.40 (1H, dd), 7.65 (1H, d), 8.01 (1H, d), 8.10 (1H, m), 8.47 (1H, brm).

Pharmacological Test Example 1 (effect on L-type and T-type Ca (calcium) channel expressed in mammalian cells (BHK cells))

Test Method

In this test, an electrophysiological evaluation was carried out by use of BHK (baby hamster kidney) cells in which L-type Ca channel or T-type Ca channel ($\alpha_{1G}$) was expressed according to the method of Wakamori M et al. (Wakamori M et al.: J Biol Chem 273, 34857-34867, 1998) based on the whole cell patch clamp method. Each Ca-ion current was measured through a patch clamp amplifier as an inward current when depolarization pulse (10 mV in L-type Ca channel, −20 mV in T-type Ca channel) was applied to cells maintained at a membrane potential of −80 mV. Optically active R-form or S-form of efonidipine was dissolved in extracellular solution and applied with perfusion. At 5 minutes after the application, any variation in Ca-ion current was measured. The results are shown in Ca current inhibition (%) of the compound of the present invention to Ca current (100%) in vehicle control.

| Ca channel type | Efonidipine R-form (mean ± SE) | | |
|---|---|---|---|
| | Concentration (μM) | Inhibition (%) | Number of experiments |
| T-type | 0.1 | 19.4 ± 4.88 | 4 |
| | 1 | 41.7 ± 5.3 | 6 |
| | 10 | 72.7 ± 5.6 | 8 |
| L-type | 10 | 2.2 ± 3.4 | 4 |

| Ca channel type | Efonidipine S-form (mean ± SE) | | |
|---|---|---|---|
| | Concentration (μM) | Inhibition (%) | Number of experiments |
| T-type | 0.1 | 7.7 | 1 |
| | 1 | 42.9 ± 8.4 | 6 |
| | 10 | 75.6 ± 7.1 | 3 |
| L-type | 1 | 55.6 ± 7.1 | 2 |

Results

The optically active R-form of efonidipine showed concentration-dependent inhibition in a concentration of 0.1 μM or more for T-type Ca channel, and did not show any inhibition for L-type Ca channel even in a concentration of 10 μM. On the other hand, the S-form showed a strong inhibition for L-type Ca channel that is as high as 55.6±7.1% in 1 μM. From these results, it was found that R-form of efonidipine has a high selectivity for T-type Ca channel.

In addition, L-type Ca channel inhibition was shown only by one optically active S-form, whereas T-type Ca channel inhibition was shown by both optically active forms to equal level. This suggests that if 1,4-dihydropyridine compound showing T-type Ca channel blocking effect in a form of racemate is found, the one (R-form) of the optically active products will be a compound having a high selectivity for T-type Ca channel.

Pharmacological Test Example 2 (effect on T-type Ca channel expressed in mammalian cells (BHK cells))

Test Method

Similarly to the procedure of Pharmacological Test Example 1, the compounds of formula

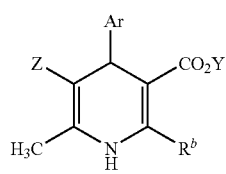

were measured for T-type Ca channel inhibition in a drug concentration of 10 μM, and the results are shown in table described below.

In the meanwhile, Z1 to Z4, Y1 to Y7, B1 and A1 to A7 used in the table mean the kind of substituents of the compounds as follows:

Z1: 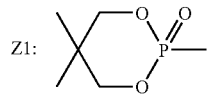   Z2: 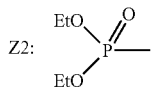

Z3: 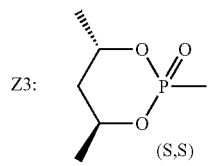 (S,S)   Z4: 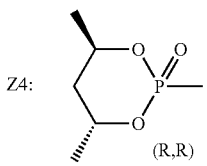 (R,R)

Y1: 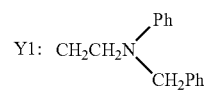   Y2: 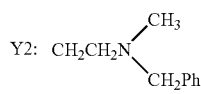

Y3: 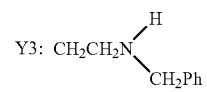   Y4: 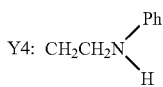

Y5: 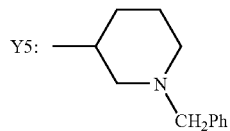   Y6: 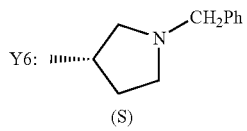 (S)

Y7: 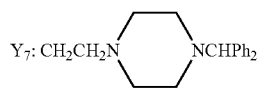

B1: CH$_2$OCH$_2$CH$_2$NH$_2$ 

A1: 3-nitropheny, A2: 3-chlorophenyl, A3: 2-nitrophenyl, A4: 2-methoxyphenyl, A5: 3-methoxyphenyl, A6: phenyl, A7: 3-trifluoromethylphenyl

| Z  | Ar | Y      | R$^b$   | 4-position configuration | Note     | Inhibition (%) | Number of experiments |
|----|----|--------|---------|--------------------------|----------|----------------|-----------------------|
| Z1 | A2 | Y1     | methyl  | racemate                 |          | 17.8           | 1                     |
| Z1 | A3 | Y1     | methyl  | racemate                 |          | 29.9           | 2                     |
| Z1 | A4 | Y1     | methyl  | racemate                 |          | 51.0           | 1                     |
| Z1 | A5 | Y1     | methyl  | racemate                 |          | 38.4           | 3                     |
| Z1 | A6 | Y1     | methyl  | racemate                 |          | 38.0           | 2                     |
| Z2 | A1 | Y1     | methyl  | racemate                 |          | 38.8           | 1                     |
| Z2 | A7 | Y2     | methyl  | racemate                 | HCl salt | 49.9           | 3                     |
| Z1 | A1 | Y3     | methyl  | racemate                 |          | 39.2           | 2                     |
| Z1 | A1 | Y4     | methyl  | racemate                 |          | 55.3           | 2                     |
| Zi | A1 | Y2     | methyl  | racemate                 |          | 77.0           | 2                     |
| Z1 | A1 | Y5     | methyl  | racemate                 |          | 39.0           | 3                     |
| Z1 | A1 | Y6     | methyl  | racemate                 |          | 41.8           | 2                     |
| Z3 | A1 | Y7     | methyl  | racemate                 | 2HCl salt| 81.0           | 4                     |
| Z4 | A1 | Y7     | methyl  | (−) form                 |          | 65.2           | 2                     |
| Z1 | A1 | Y7     | methyl  | racemate                 |          | 47.3           | 2                     |
| Z1 | A2 | methyl | B1      | racemate                 |          | 29.9           | 1                     |

As the above-mentioned compounds in a form of racemate showed T-type calcium channel inhibition, it is assumed that the one of the optically active product (R-form shows no L-type calcium channel inhibition) becomes a compound showing a selective T-type calcium channel inhibition.

Preparation Example 1

Granules containing the following components were prepared.

| Components | |
|---|---|
| Compound of formula (1) | 10 mg |
| Lactose | 700 mg |
| Cornstarch | 274 mg |
| HPC-L | 16 mg |
| | 1000 mg |

The compound of formula (I) and lactose were passed through 60-mesh sieve. Cornstarch was passed through 120-mesh sieve. These components were mixed in a twin-cylinder mixer. Hydroxypropylcellulose having a low viscosity (HPC-L) was added to the mixed powders, the resulting mixture was kneaded, granulated (extrusion granulation, bore 0.5 to 1 mm), and then dried. The obtained dried granules were passed through a vibrating screen (12/60 mesh) to obtain an intended granules.

Preparation Example 2

Powders for filling into capsules containing the following components were prepared.

| Components | |
|---|---|
| Compound of formula (1) | 10 mg |
| Lactose | 79 mg |
| Cornstarch | 10 mg |
| Magnesium stearate | 1 mg |
| | 100 mg |

The compound of formula (I) and lactose were passed through 60-mesh sieve. Cornstarch was passed through 120-mesh sieve. These components were mixed with magnesium stearate in a twin-cylinder mixer. 100 mg of 10 times powders were filled into No. 5 hard gelatin capsule.

Preparation Example 3

Granules for filling into capsules containing the following components were prepared.

| Components | |
|---|---|
| Compound of formula (1) | 15 mg |
| Lactose | 90 mg |
| Cornstarch | 42 mg |
| HPC-L | 3 mg |
| | 150 mg |

The compound of formula (I) and lactose were passed through 60-mesh sieve. Cornstarch was passed through 120-mesh sieve. These components were mixed in a twin-cylinder mixer. Hydroxypropylcellulose having a low viscosity (HPC-L) was added to the mixed powders, the resulting mixture was kneaded, granulated, and then dried. The obtained dried granules were passed through a vibrating screen (12/60 mesh) to obtain an intended granules. 150 mg of the granules were filled into No. 4 hard gelatin capsule.

Preparation Example 4

Tablets containing the following components were prepared.

| Components | |
|---|---|
| Compound of formula (1) | 10 mg |
| Lactose | 90 mg |
| Fine crystalline cellulose | 30 mg |
| Magnesium stearate | 5 mg |
| CMC-Na | 15 mg |
| | 150 mg |

The compound of formula (1), lactose, fine crystalline cellulose and CMC-Na (carboxymethylcellulose sodium salt) were passed through 60-mesh sieve and mixed one another. Magnesium stearate was added to the mixed powders to obtain mixed powders for preparation. The powders were subjected to direct compression to obtain 150 mg of tablets.

Preparation Example 5

Intravenous preparations were prepared as follows.

| | |
|---|---|
| Compound of formula (1) | 100 mg |
| Saturated fatty acid glyceride | 1000 ml |

Generally, the solution containing the above-mentioned components was intravenously administered to a patient in a rate of 1 ml per minute.

INDUSTRIAL APPLICABILITY

As the compounds of the present invention have selective T-type calcium channel blocking effect, it is assumed that these compounds can be used for therapy of hypercardia, heart failure, cardiomyopathy, tachycardia-arrhythmia represented by atrial fibrillation, arterial sclerosis, renal disorder represented by nephritis/nephropathy, renal insufficiency, inflammation and edema, hyper-aldosteronism, neurogenic pain, or epilepsy, without adverse effect on blood pressure, cardiac function and Quality of Life. Therefore, the present invention can provide therapeutic agents for the above-mentioned diseases with effectiveness, safety and Quality of Life, and thus it is very useful for example in the art of medical treatment and medicine.

The invention claimed is:

1. A method of treating renal injury, the method comprising:
administering to a human patient in need thereof, an effective amount of a T-type calcium channel blocker, and a pharmaceutically acceptable excipient, wherein the T-type calcium channel blocker is an optically active 1,4-dihydropyridine compound or a pharmaceutically acceptable salt thereof, of formula (1)

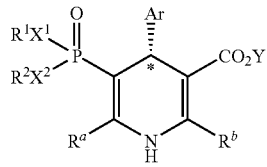
(1)

wherein:
$R^1$ and $R^2$ are independently of each other a $C_{1-6}$ alkyl group, or
$R^1$ and $R^2$ together form —$CR^5R^6$—$CR^7R^8$—$CR^9R^{10}$—,
wherein:
$R^5$ to $R^{10}$ are independently of each other a hydrogen atom or a $C_{1-6}$ alkyl group;
$X^1$ and $X^2$ are O;
Ar is a phenyl group that is unsubstituted or is substituted with one or two substituents selected from the group consisting of $NO_2$, $CF_3$, Cl, and $OR^{14}$, wherein $R^{14}$ is a $C_{1-6}$ alkyl group;
$R^a$ and $R^b$ are independently of each other a $C_{1-6}$ alkyl group, or $CH_2O$—$L^2$—$NR^{16}R^{17}$, wherein $R^{16}$ and $R^{17}$ are a hydrogen atom, and $L^2$ is a $C_{2-6}$ alkylene group;
Y is:
a $C_{1-20}$ alkyl group,
—$L^3$—$NR^{18}R^{19}$,

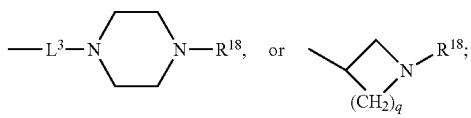

wherein:
$R^{18}$ and $R^{19}$ are independently of each other a phenyl group, or a $C_{1-6}$ alkyl group that is unsubstituted or is substituted with a phenyl group,
$L^3$ is a $C_{2-6}$ alkylene group, and
q is 2 or 3; and
* is an absolute configuration of R.

2. A method of treating hyperaldosteronism, the method comprising:
administering to a human patient in need thereof, an effective amount of a T-type calcium channel blocker, and a pharmaceutically acceptable excipient, wherein the T-type calcium channel blocker is an optically active 1,4-dihydropyridine compound or a pharmaceutically acceptable salt thereof, of formula (1)

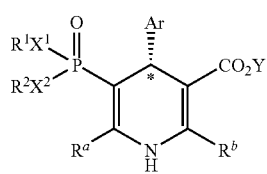
(1)

wherein:
$R^1$ and $R^2$ are independently of each other a $C_{1-6}$ alkyl group, or
$R^1$ and $R^2$ together form —$CR^5R^6$—$CR^7R^8$—$CR^9R^{10}$—,
wherein:
$R^5$ to $R^{10}$ are independently of each other a hydrogen atom or a $C_{1-6}$ alkyl group;
$X^1$ and $X^2$ are O;
Ar is a phenyl group that is unsubstituted or is substituted with one or two substituents selected from the group consisting of $NO_2$, $CF_3$, Cl, and $OR^{14}$, wherein $R^{14}$ is a $C_{1-6}$ alkyl group;
$R^a$ and $R^b$ are independently of each other a $C_{1-6}$ alkyl group, or $CH_2O$—$L^2$—$NR^{16}R^{17}$, wherein $R^{16}$ and $R^{17}$ are a hydrogen atom, and $L^2$ is a $C_{2-6}$ alkylene group;
Y is:
a $C_{1-20}$ alkyl group,
—$L^3$—$NR^{18}R^{19}$,

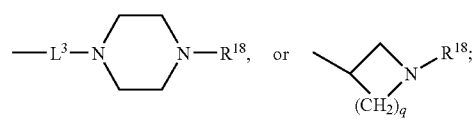

wherein:
$R^{18}$ and $R^{19}$ are independently of each other a phenyl group, or a $C_{1-6}$ alkyl group that is unsubstituted or is substituted with a phenyl group,
$L^3$ is a $C_{2-6}$ alkylene group, and
q is 2 or 3; and
* is an absolute configuration of R.

3. A method of treating neuropathic pain, the method comprising:
administering to a human patient in need thereof, an effective amount of a T-type calcium channel blocker, and a pharmaceutically acceptable excipient, wherein the T-type calcium channel blocker is an optically active 1,4-dihydropyridine compound or a pharmaceutically acceptable salt thereof, of formula (1)

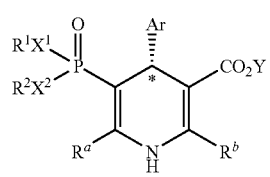
(1)

wherein:
$R^1$ and $R^2$ are independently of each other a $C_{1-6}$ alkyl group, or
$R^1$ and $R^2$ together form —$CR^5R^6$—$CR^7R^8$—$CR^9R^{10}$—,
wherein:
$R^5$ to $R^{10}$ are independently of each other a hydrogen atom or a $C_{1-6}$ alkyl group;
$X^1$ and $X^2$ are O;
Ar is a phenyl group that is unsubstituted or is substituted with one or two substituents selected from the group consisting of $NO_2$, $CF_3$, Cl, and $OR^{14}$, wherein $R^{14}$ is a $C_{1-6}$ alkyl group;

$R^a$ and $R^b$ are independently of each other a $C_{1-6}$ alkyl group, or $CH_2O-L^2-NR^{16}R^{17}$, wherein $R^{16}$ and $R^{17}$ are a hydrogen atom, and $L^2$ is a $C_{2-6}$ alkylene group;

Y is:
 a $C_{1-20}$ alkyl group,
 $-L^3-NR^{18}R^{19}$,

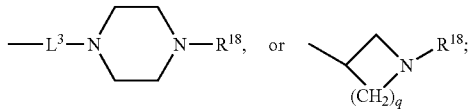

wherein:

$R^{18}$ and $R^{19}$ are independently of each other a phenyl group, or a $C_{1-6}$ alkyl group that is unsubstituted or is substituted with a phenyl group,
$L^3$ is a $C_{2-6}$ alkylene group, and
q is 2 or 3; and
* is an absolute configuration of R.

4. The method of claim 1, wherein Y is:
 a $C_{1-20}$ alkyl group,
 $-L^3-NR^{18}R^{19}$, or

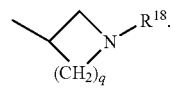

5. The method of claim 2, wherein Y is:
 a $C_{1-20}$ alkyl group,
 $-L^3-NR^{18}R^{19}$, or

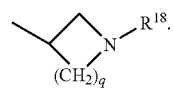

6. The method of claim 3, wherein Y is:
 a $C_{1-20}$ alkyl group,
 $-L^3-NR^{18}R^{19}$, or

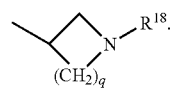

* * * * *

UNITED STATES PATENT AND TRADEMARK OFFICE
CERTIFICATE OF CORRECTION

| | | |
|---|---|---|
| PATENT NO. | : 7,563,782 B2 | Page 1 of 1 |
| APPLICATION NO. | : 10/549510 | |
| DATED | : July 21, 2009 | |
| INVENTOR(S) | : Masuda et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 262 days.

Delete the phrase "by 262 days" and insert -- by 648 days --

Signed and Sealed this

Fourth Day of May, 2010

David J. Kappos
*Director of the United States Patent and Trademark Office*